United States Patent

Heinemann et al.

[11] 4,442,102
[45] Apr. 10, 1984

[54] 1,5-DIPHENYLPYRAZOLIN-3-ONE COMPOUNDS, PROCESS AND INTERMEDIATES FOR PREPARATION THEREOF AND PHARMACEUTICAL COMPOSITIONS CONTAINING SAME

[75] Inventors: Henning Heinemann, Hanover, Fed. Rep. of Germany; Daniel Jasserand, Paris, France; Wolfgang Milkowski, Burgdorf, Fed. Rep. of Germany; Dimitri Yavordios, Chatillon-sur-Chalaronne, France; Horst Zeugner, Hanover, Fed. Rep. of Germany

[73] Assignee: Kali-Chemie Pharma GmbH, Hanover, Fed. Rep. of Germany

[21] Appl. No.: 409,631

[22] Filed: Aug. 19, 1982

[30] Foreign Application Priority Data

Aug. 20, 1981 [DE] Fed. Rep. of Germany ....... 3132915

[51] Int. Cl.³ .................. C07D 403/06; C07D 231/08; A61K 31/495
[52] U.S. Cl. .................................... 424/250; 544/364; 544/371; 548/372
[58] Field of Search ................. 544/364, 371; 424/250

[56] References Cited

U.S. PATENT DOCUMENTS 3,169,966 2/1965 Schmidt et al. ..................... 544/364

*Primary Examiner*—Donald G. Daus
*Assistant Examiner*—S. A. Gibson
*Attorney, Agent, or Firm*—Schwartz, Jeffery, Schwaab, Mack, Blumenthal & Koch

[57] ABSTRACT

New 1,5-diphenylpyrazolin-3-one compounds and a method of preparing them are described. The compounds have the general formula I

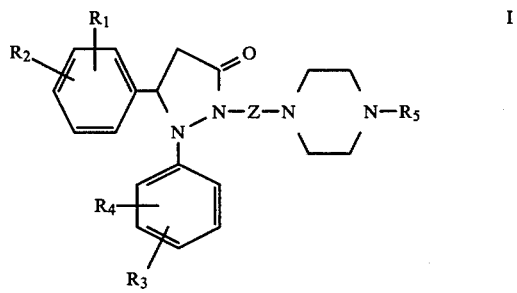

where $R_1$ is a hydrogen or halogen atom, or a lower alkyl, lower alkoxy, hydroxy, trifluoromethyl or lower alkanoyloxy radical, $R_2$ is a hydrogen or halogen atom, or a lower alkyl, or lower alkoxy radical, or $R_1$ and $R_2$ are bonded to adjacent carbon atoms and together denote a methylenedioxy or ethylenedioxy radical, $R_3$ is a hydrogen or halogen atom, or a lower alkyl, lower alkoxy, hydroxy, trifluoromethyl or lower alkanoyloxy radical, $R_4$ is a hydrogen or halogen atom, or a lower alkyl, lower alkoxy radical, or $R_3$ and $R_4$ are bonded to adjacent carbon atoms and together denote a methylenedioxy or ethylenedioxy radical, Z is an alkylene radical with 2 to 6 carbon atoms and $R_5$ is an optionally substituted pyridyl radical, a thienyl radical or an optionally substituted phenyl radical. The compounds have pharmacological properties, for example antiallergic properties.

5 Claims, No Drawings

1,5-DIPHENYLPYRAZOLIN-3-ONE COMPOUNDS, PROCESS AND INTERMEDIATES FOR PREPARATION THEREOF AND PHARMACEUTICAL COMPOSITIONS CONTAINING SAME

BACKGROUND OF THE INVENTION

This invention relates to novel 2-piperazinoalkyl-1,5-diphenylpyrazolin-3-one compounds and salts thereof, and to pharmaceutical preparations containing these compounds and to a method for preparing these compounds, as well as intermediate products useful in the method.

SUMMARY OF THE INVENTION

It is an object of the invention to provide novel 1,5-diphenylpyrazolin-3-one compounds with valuable pharmacological properties, and a method for their preparation.

It has now been found that the novel 1,5-Diphenylpyrazolin-3-one compounds have valuable pharmacological properties, in particular pronounced antiallergic properties, and in addition also have hypotensive properties and an advantageous action profile with a wide therapeutic range and low toxicity. On the basis of these properties, the new compounds are suitable as medicaments for the treatment of allergic illnesses, such as, for example, asthma or hay fever or allergic origin.

According to one aspect of the present invention there is provided a 1,5-diphenylpyrazolin-3-one compound of the general formula I

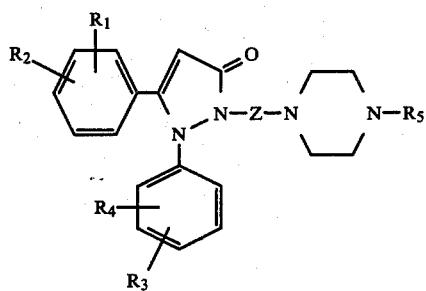

where $R_1$ is a hydrogen or halogen atom, or a lower alkyl, lower alkoxy, hydroxyl, trifluoromethyl or lower alkanoyloxy radical, $R_2$ is a hydrogen or halogen atom, or a lower alkyl or lower alkoxy radical, or $R_1$ and $R_2$ are bonded to adjacent carbon atoms and together denote a methylenedioxy or ethylenedioxy radical, $R_3$ is a hydrogen or halogen atom, or a lower alkyl, lower alkoxy, hydroxyl, trifluoromethyl or lower alkanoyloxy radical, $R_4$ is a hydrogen or halogen atom, or a lower alkyl or lower alkoxy radical, or $R_3$ and $R_4$ are bonded to adjacent carbon atoms and together denote a methylenedioxy or ethylenedioxy radical, Z is an alkylene radical with 2 to 6 carbon atoms, and $R_5$ is an unsubstituted pyridyl radical, a pyridyl radical which is monosubstituted by a halogen atom or a lower alkyl or lower alkoxy radical, a thienyl radical, or an unsubstituted or substituted phenyl radical a

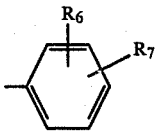

where $R_6$ is a hydrogen or halogen atom, or a lower alkyl lower alkoxy, hydroxyl, trifluoromethyl or lower alkanoyloxy radical, and $R_7$ is a hydrogen, or halogen atom, or a lower alkyl or lower alkoxy radical, or $R_6$ and $R_7$ are bonded to adjacent carbon atoms and together denote a methylenedioxy or ethylenedioxy radical: and acid addition salts thereof.

If the substituents $R_1$ to $R_4$ on the phenyl rings and the substituents contained in the radical $R_5$ in the compounds of the formula I contain a lower alkyl group, this can be straight-chain or branched and preferably contains 1 to 4 carbon atoms. Possible substituents are thus, in particular, methyl, ethyl, n-propyl, isopropyl, n-butyl or tert.-butyl, preferably methyl, ethyl, n-propyl and isopropyl radicals. Preferred alkyl radicals are ethyl and, in particular, methyl radicals, especially in the case of disubstitution of the phenyl rings. Lower alkoxy substituents are preferably methoxy or ethoxy radicals.

Preferred halogen substituents in the phenyl rings and/or in a pyridyl ring are, fluorine, chlorine and bromine. If a phenyl ring is substituted by a trifluoromethyl radical, monosubstitution is preferred. Mono- or di-substitution is advantageous in the case of halogen atoms and/or alkyl or and/or alkoxy substituents.

The radical Z is a straight or branched alkylene chain with 2 to 6 carbon atoms, alkylene chains with 2 to 4 carbon atoms being preferred.

If $R_5$ is a pyridyl group, this can be bonded to the rest of the molecule in the 2-, 3- or 4-position, preferably in the 2-position. The pyridyl group can be unsubstituted or substituted by one of the abovementioned substituents, in particular lower alkyl or alkoxy, preferably methyl or methoxy.

If $R_5$ is a thienyl radical, this can be bonded to the rest of the molecule in the 2- or 3-position, preferably in the 2-position.

According to another aspect of the present invention, the aforesaid 1,5-diphenylpyrazolin-3-one compound of formula I, or an acid addition salt thereof, is prepared by a method in which, in a manner which is known per se, either (a) a compound of formulae II or III

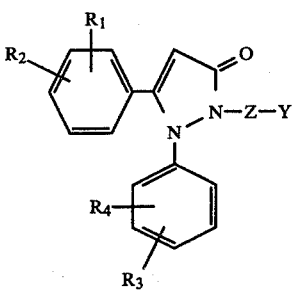

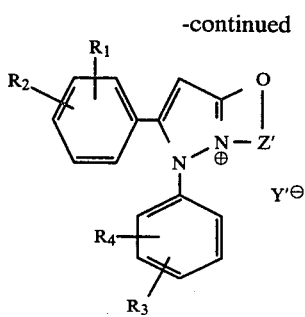
III where $R_1$, $R_2$, $R_3$, $R_4$ and Z have the above defined meanings, Y is a radical which can be split off by aminolysis, Z' is an alkylene chain with 2 to 4 carbon atoms, and Y' is a halogen atom, or a mixture of such compounds is reacted with a compound of formula V

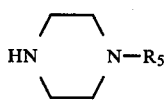
V where $R_5$ has the above defined meaning, or (b) in order to prepare a compound of formula Ia

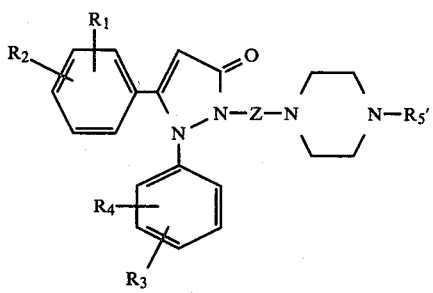
Ia where $R_1$, $R_2$, $R_3$, $R_4$ and Z have the above defined meanings and $R_5'$ is a substituted phenyl group a'

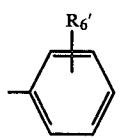
a' where $R_6'$ is a trifluoromethyl radical in the ortho- or para-position, a compound of the formula IV

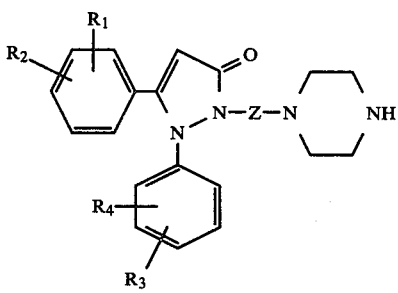
IV where $R_1$, $R_2$, $R_3$, $R_4$ and Z have the above defined meanings, is reacted with a compound of formula VI

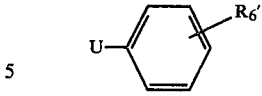
VI where $R_6'$ has the above defined meaning and U is a halogen atom. If the compound of formula I is obtained in the form of the free compound it may be subsequently converted into an acid addition salt or if the compound of formula I is obtained in the form of an acid addition salt it may be subsequently converted into the free compound.

DETAILED DESCRIPTION OF THE INVENTION

The reaction of the compounds of formulae II or III or the mixture thereof with a compound of formula V according to process variant (a) can be carried out by methods which are customary per se for the alkylation of amines.

The reaction is advantageously carried out under basic conditions in an organic solvent which is inert under the reaction conditions. Possible radicals which can be split off by aminolysis from a compound of formula II are, in particular, halogens, such as chlorine, bromine or iodine, preferably chlorine or bromine. Examples of suitable solvents which may be used include aromatic hydrocarbons, such as benzene, toluene or xylene, cyclic ethers, such as dioxane, dimethylformamide, 1,3-dimethyl-2-imidazolidinone, hexamethylphosphoric acid triamide, sulpholane, dimethylsulphoxide, tetramethylurea and lower alkanols, for example isopentanol. The temperature can be from room temperature up to 150° C., elevated temperature, for example a temperature of from 50° to 150° C., in particular from 90° to 150° C., advantageously being used if a compound of formula II is employed, whilst a temperature from room temperature to the boiling point of the solvent can be used if a compound of formula III is employed. If desired, the reaction of the compound of formulae II or III with the compound of formula V can, however, also take place in the melt without a solvent. The reaction can advantageously be carried out with the addition of an organic or inorganic base. However, it is also possible to employ an excess of the compound of formula V and to use this as an internal base. Particularly suitable organic bases include alkali metal carbonates or bicarbonates, such as sodium carbonate, sodium bicarbonate or potassium carbonate. Suitable organic bases include tertiary organic amines, in particular tertiary lower alkylamines, such as triethylamine, n-tripropylamine, n-tributylamine, 1,4-dimethylpiperazine or pyridine.

If the compounds of formulae II, III or V contain free hydroxyl groups as substituents, these are advantageously provided with a protective group, in a manner which is known per se, during the reaction. Suitable protective groups which can easily be split off again after the reaction are known from, for example E. McOmie "Protective Groups in Organic Chemistry" Plenum Press 1971. For example, ethers, in particular tetrahydropyranyl ethers, are suitable for protecting a hydroxyl group. These protective groups can easily be removed again in a known manner after the reaction.

The reaction of a compound of formula IV with a compound of formula VI can likewise be carried out in a manner which is known per se, under the conditions customary for alkylation of amines, for example the conditions mentioned above for the reaction of a compound of formula II with a compound of formula V. The substituted halogenated phenyl compounds are sufficiently activated by the presence of a second order substituent to be capable of reaction with the piperazine derivative of formula IV.

The compound of formula I can be isolated from the reaction mixture, and purified, in a manner which is known per se. If the compound is obtained in the form of an acid addition salt, this salt can be converted into the free base in the customary manner, and, where desired, the base can be converted into a pharmacologically acceptable acid addition salt in known manner.

Examples of suitable pharmacologically acceptable acid addition salts of the compounds of formula I are their salts with hydrochloric acid, hydrobromic acid, sulphuric acid, phosphoric acid, methanesulphonic acid, ethanesulphonic acid, benzenesulphonic acid, p-toluenesulphonic acid, citric acid, acetic acid, lactic acid, succinic acid, maleic acid, fumaric acid, malic acid, tartaric acid, benzoic acid, phenylacetic acid and mandelic acid.

The compounds of formula I contain two or if $R_5$ denotes an optionally substituted pyridyl group, three basic centres and can thus form acid addition salts with one, two or three equivalents of acid. Mono-acid salts are particularly suitable for the preparation of pharmaceutical compositions. Salts which contain several equivalents of acid can, if desired, be converted into mono-acid salts in a manner which is known per se, for example by conversion into the free base and subsequent reaction of the base with an equivalent amount of acid.

Compounds of formula I in which Z is a branched alkylene chain are obtained, in the synthesis, in the form of their racemates. The racemic mixtures as well as the optically active forms of these compounds fall within the scope of this invention. The racemic mixtures can be separated into their optically active antipodes in a manner which is known per se, by reaction with suitable optically active acids, such as, for example, O,O'-dibenzoyl-tartaric acid, mandelic acid or di-O-isopropylidene-2-oxo-L-gulonic acid, and subsequent fractional crystallisation of the salts obtained (Tetrahedron 33, (1977) 2725–2736).

Compounds of formulae II and III have not yet been described in the Literature, and represent new, valuable intermediate products for the preparation of pharmacologically active compounds, for example the compounds of formula I.

Compounds of formulae II and III can be obtained by processes which are known per se. Thus, in particular, compounds of formula II where Y is a halogen atom and compounds of formula III can be obtained by reacting alkali metal salts, prepared in situ, of a 1,5-diphenyl-pyrazolin-3-one compound of formula VIII

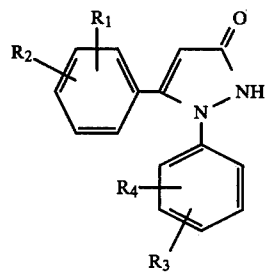

where $R_1$, $R_2$, $R_3$ and $R_4$ have the above defined meanings, with a compound of formula VII

Y—Z—Y'  VII where Z and Y have the above defined meanings and Y' is a halogen atom, Y' preferably being chlorine or bromine.

The reaction is advantageously carried out in a solvent which is inert under the reaction conditions, at a temperature of from 0° C. to the boiling point of the solvent. In general, a temperature of from 0° C. to 100° C. is preferred. Examples of suitable solvents are lower alcohols, such as methanol, ethanol, isopropanol, butanol and tert-butanol, as well as aromatic hydrocarbons, such as benzene and toluene, dimethylformamide, sulpholane, hexamethylphosphoric acid triamide, tetramethylurea and cyclic ethers, such as, for example dioxane and tetrahydrofuran.

Possible alkali metal salts of the 1,5-diphenylpyrazolin-3-one compounds are the lithium, sodium or potassium salts, preferably the sodium salt, and these salts may be obtained in situ by reacting the compound of formula VIII with an alkali metal alcoholate or alkali metal hydride.

If Z in the compound of formula VIII is an alkylene chain with 2 to 4 carbon atoms, cyclic alkylation products of formula III are obtained in the reaction in addition to the open-chain alkylation products of formula II. The reaction mixture contains varying proportions of the compounds II and III, depending upon the solvents and alkali metal compounds used, the reaction time and the particular meanings of the individual substituents. Thus, for example, if a lower alcohol and the corresponding alkali metal alcoholate are used and the reaction times are relatively long, for example 12 to 35 hours, the cyclic compounds III are predominantly formed, whilst the compounds II are predominantly formed if dimethylformamide and alkali metal hydrides are used and the reaction times are, for example, 1 to 5 hours. Since both the compounds II and III or mixtures thereof can be used in the subsequent reaction, it is not necessary to separate the two compounds before further reaction. The cyclic compounds III can, however, of course be separated from the open-chain products by crystallisation in a manner which is known per se. Thus, the cyclic immonium salts III can easily be crystallised from, for example, aromatic and/or halogenated hydrocarbons, such as benzene, toluene or chloroform.

In general, alkylation of 1,5-diphenylpyrazolin-3-one compound of formula VIII with the compound of formula VII gives a mixture of the desired N-alkylated product and the corresponding isomeric O-alkylated product. The N-alkylated product can be separated off from the mixture by chromatography or crystallisation.

The O-alkylated by products can be rearranged into the corresponding N-alkylated products II and the cyclic immonium salts III simply by heating. The rearrangement temperature is advantageously from 60° C. to 200° C. If desired, the rearrangement can be carried out in the presence of an inert solvent, advantageously at the boiling point of the solvent. Suitable solvents are lower alcohols with boiling points within the range given, for example methanol, butanol or isopentanol, and aromatic hydrocarbons with boiling points within the range given, such as benzene, toluene or xylene. The mixture of cyclic immonium compound III, N-alkylated product II and isomeric O-alkylated product, obtained during alkylation, can also be employed directly without prior separation, for the rearrangement reaction under the influence of heat.

Compounds of formula IV have not yet been described in the Literature, and are also new valuable intermediate products for the preparation of pharmacologically active compounds, for example the compounds of formula I.

Compounds of formula IV can be obtained by methods which are known per se, for example by reacting a compound of formulae II or III with an excess of piperazine. The reaction can be carried out by methods which are customary per se for the alkylation of amines, for example under the conditions described above for the reaction of a compound of formulae II or III with a compound of formula V.

Compounds of formula IV can also be obtained from compounds of formula IX

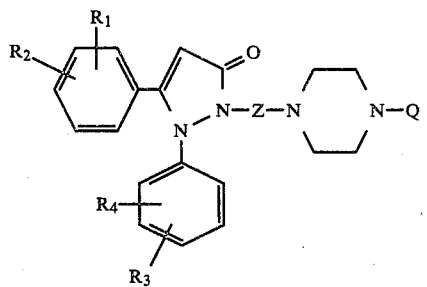

IX where $R_1$, $R_2$, $R_3$, $R_4$ and Z have the above defined meanings and Q represents an amine-protecting group, by splitting off the amine-protecting group in a manner which is known per se. Possible amine-protecting groups are the customary protecting groups which are known per se for the protection of an amino group, for example acyl groups which can be split off by hydrolysis or benzyl groups which can be split off by hydrogenolysis. Suitable protective groups are known from, for example, E. McOmie "Protective Groups in Organic Chemistry"; Plenum Press, London (1971), page 44 et seq., the formyl group and lower carbalkoxy protecting groups being particularly suitable. These groups can be split off by acid or alkaline hydrolysis in a manner which is known per se.

Compounds of formula IX can be obtained in a manner which is known per se, for example by reacting a compound of formulae II or III with a compound of formula X

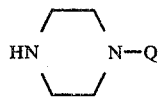

X where Q has the above defined meanings. The reaction can be carried out by methods which are customary for the alkylation of amines, for example under the reaction conditions described for the reaction of a compound of formulae II or III with a compound of formula V.

The 1,5-diphenyl-pyrazolin-3-ones of formula VIII are known, or they can be prepared by methods which are known per se, for example by the methods described by Michaelis and Rassmann (Ann. 352, (1907) 158) and by Michaelis and Willert (Ann. 358, (1908) 159), for example starting from correspondingly substituted benzoylacetic acid esters and correspondingly substituted β-acetylphenyl-hydrazines.

Compounds of formula V are known, or they can be prepared by methods which are known per se, for example by reacting an amine of formula XI $H_2N-R_5$  XI where $R_5$ has the above defined meaning, with a corresponding di-(haloalkyl)amine, under conditions which are customary for the alkylation of amines.

The compounds of formula I and their pharmacologically acceptable acid addition salts are distinguished by interesting pharmacological properties, and in particular have antiallergic actions. In addition, the compounds are well tolerated and are only slightly toxic, and, in particular, there is a wide interval between their therapeutically effective dose and the toxic dose.

On the basis of their antiallergic actions, the compounds of formula I and their pharmacologically acceptable acid addition salts are suitable as antiallergic agents for the treatment of allergic illnesses, such as, for example, bronchial asthma or allergic rhinitis.

The antiallergic properties of the compounds of formula I can be demonstrated in standard pharmacological tests on small animals. For example, the substances have an inhibiting action on the release of endogenic mediators from mast cells or basophilic leucocytes which leads to allergic reactions. The doses to be used vary, of course, depending on the nature of the substance used, on the mode of administration and on the condition to be treated. In general, however, satisfactory results are achieved in animal experiments with doses of from 0.05 to 75 mg. per kg of body weight. Thus, the new compounds exhibit a specific inhibiting action in the PCA test (Passive Cutaneous Anaphylaxis test) on rats which is described below.

Description of the test method to determine the inhibition of passive cutaneous anaphylaxis (PCA test, see Arch.int. pharmacology 252 (1981) 316–326).

To prepare the IgE-antiovoalbumin serum, used in the test, by the method of Mota (Immunology 7, (1964) 681) and J. Goose (Immunology 16 (1969) 749), male Wistar rats of 200–250 g. body weight were sensitised by subcutaneous injection of 1 mg. of ovoalbumin and 1 ml. of Bordatella pertussis suspension ("Vaxicoq" Merieux $3.10^{10}$ organisms/ml.). After 14 days, the animals are exsanguinated and the blood is centrifuged. The antiserum thus obtained is stored at 20° C.

Non-sensitised rats are injected, in each case, with 0.1 ml. of antiserum into the skin at four different places on their shaven backs. After 72 hours, a solution of the test compound or, for comparison, only the solvent, is administered orally, and 10 minutes later, 5 mg. of ovoalbumin and 5 mg. of blue dyestuff (Evans blue) in 0.9% strength NaCl solution are administered intraperitoneally. After 30 minutes, the animals are sacrificed and the diameters of the blue spots formed at the sites injected with antiserum are measured. The inhibiting effect of the test substance is determined from the size of the blue spots which appear.

The table which follows shows the results obtained in the test described above. The example numbers given for the compounds of the formula I relate to the preparation Examples below.

| Test substance of formula I Example No. | PCA inhibition Ed$_{50}$ mg/kg p.o. |
| --- | --- |
| 1 | 0.8 |
| 13 | 8.5 |
| 22 | 9.8 |
| 27 | 8.2 |

Determination of the minimum toxic dose in mice: it was not possible to detect any toxic symptoms on oral administration of the above substances in doses of up to 300 mg/kg.

As medicines, the compounds of the formula I and their pharmacologically acceptable salts can be compounded as conventional pharmaceutical preparations, such as, for example, tablets, capsules, suppositories or solutions, together with the customary solid or liquid diluents or carriers, together with any necessary or desirable pharmaceutical auxiliaries. These pharmaceutical preparations can be made by methods which are known per se, using the customary solid excipients, such as, for example, talc, lactose or starch, or liquid diluents, such as, for example, water, fatty oils or liquid paraffins.

The compounds of formula I can be administered in pharmaceutical use forms which contain about 0.5 to 100 mg. preferably 0.5–25 mg., of active substance per individual dose. The dosage to be used will, of course, vary depending on the species to be treated and the individual requirements. Parenteral formulations will in general contain less active substance than preparations for oral administration.

The Examples which follow are non-limiting Examples intended to illustrate the preparation of the new compounds of formula I and of the new intermediate products in more detail.

The structures of the new compounds were confirmed by spectroscopic investigations, in particular by precise analysis of the IR and NMR spectra.

The IR spectra of the 1,5-diphenylpyrazolin-3-one compounds show the carbonyl absorption band of the pyrazolin-3-one ring at about 1630–1680 cm$^{-1}$, and are free from —C≡N bands, which can be observed in pyrazole derivatives.

EXAMPLE 1

1,5-Diphenyl-2-{3-[4-(2-pyridyl)-piperazin-1-yl]-propyl}-pyrazolin-3-one (A) 47.2 g. (200 mmols) of 1,5-diphenylpyrazolin-3-one are dissolved in 350 ml. of dimethylformamide. 6.6 g. of sodium hydride (80% pure, 220 mmols) are added in portions to the solution at 80° C., whilst stirring. The resulting suspension is allowed to cool to 60° C., and a solution of 34.7 g. (220 mmols) of 1-bromo-3-chloropropane in 150 ml. of dimethylformamide is added dropwise. During this addition, the temperature drops to about 40° C. Stirring is continued at this temperature for 12 hours. As much as possible of the dimethylformamide is then stripped off under reduced pressure (oil pump), during which unreacted bromochloropropane is also removed from the reaction mixture. The residue is taken up in methylene chloride and the mixture is stirred. Sodium bromide and unreacted diphenylpyrazolinone are thereby precipitated, and can be filtered off with suction. The methylene chloride solution is washed with water, dried over sodium sulphate and filtered and the solvent is stripped off under reduced pressure. 60 g of a viscous, light yellow oil which contains a mixture of the isomers 1,5-diphenyl-2-(3-chloropropyl)-pyrazolin-3-one and 1,5-diphenyl-3-(3-chloropropoxy)-pyrazole remain. The latter is rearranged into 1,5-diphenyl-2-(3-chloropropyl)-pyrazolin-3-one by heating the mixture to 170° C. for one hour. The resulting product can be employed in the next reaction stage without further purification.

(B) 31.3 g of 1,5-diphenyl-2-(3-chloropropyl)-pyrazolin-3-one are dissolved in 300 ml of toluene, and 16.3 g of N-(2-pyridyl)-piperazine and 15.9 g of potassium carbonate are added to the solution. The suspension is heated under reflux for 20 hours, whilst stirring. After the reaction mixture has been cooled, it is extracted by shaking with water, the organic phase is concentrated as far as possible under reduced pressure, the residue is taken up in dilute hydrochloric acid and the suspension thus obtained is extracted with methylene chloride. The now clear aqueous phase is rendered alkaline with dilute sodium hydroxide solution and extracted with ethyl acetate. The organic extract is dried over sodium sulphate and filtered and the filtrate is evaporated under reduced pressure. 42.4 g of the title compound remain as the residue, as a light yellow oil.

To form the trihydrochloride of the title compound; this residue is dissolved in isopropyl alcohol, and a saturated solution of hydrogen chloride in diethyl ether is added dropwise to the solution, whilst stirring. The trihydrochloride crystals which have precipitated are filtered off with suction and rinsed with isopropyl alcohol and ether. Yield: 41.6 g. Melting point: 196°–198° C.

EXAMPLE 2

1,5-Diphenyl-2-{3-[4-(2-pyridyl)-piperazin-1-yl]-propyl}-pyrazolin-3-one (A) 118 g of 1,5-diphenylpyrazolin-3-one are suspended in 1 l of methanol, and a solution of 99 g of sodium methylate in methanol (30% strength solution) is added, whilst stirring. After 15 minutes, 54 ml of 1-bromo-3-chloropropane are added dropwise to the resulting clear solution, and the solution is heated under reflux for 48 hours. Most of the solvent is then distilled off under reduced pressure, the residue is dissolved in 1 l of methylene chloride and the organic solution is washed with two 250 ml portions of water. The wash water is extracted once more with 300 ml of methylene chloride and the organic phases are combined, dried over sodium sulphate and filtered. After the solvent has been stripped off under reduced pressure, 150 g of crude 1,5-diphenylpyrazolo-[2,3-b]-dihydro-1,3-oxazinium chloride remain as a yellowish crystalline residue. This residue is suspended in 200 ml of acetone and the suspension is heated under reflux for 5 minutes and then cooled, whilst stirring. The crystals are filtered off and washed again, with 250 ml of ethyl acetate, in the same way. The crystals are then dried at 60° C. in a drying chamber for 5 hours. Melting point: 208°–210° C., yield: 102 g.

(B) 156.3 g of 1,5-diphenylpyrazolo-[2,3-b]-dihydro-1,3-oxazinium chloride are suspended in 1.5 l of toluene, 165 g of potassium carbonate are added and the suspension is heated to 50° C. 77 ml of 1-(2-pyridyl)-piperazine are added dropwise in the course of 10 minutes, whilst stirring, and the reaction mixture is then heated under reflux for 5 hours. After it has been cooled, it is acidified with 650 ml of 15% strength aqueous hydrochloric acid and the aqueous phase is separated off from the organic phase and washed with 300 ml of ethyl acetate. The organic phases are discarded. A solution of 175 g of sodium hydroxide in 175 ml of water is added to the aqueous phase and the mixture is extracted with three 250 ml portions of methylene chloride. The combined methylene chloride phases are dried over sodium sulphate and filtered. After the solvent has been removed under reduced pressure, 225 g of crude 1,5-diphenyl-2-{3-[4-(2-pyridyl)-piperazin-1-yl]-propyl}-pyrazolin-3-one remain as a yellow oil. This is dissolved in 4.5 l of isopropanol. An excess of hydrogen chloride gas is then passed in, whilst stirring, and the mixture is stirred for 1 hour. The crystalline precipitate formed is filtered off, washed with two 250 ml portions of isopropanol and dried at 60° C. in a drying chamber for 12 hours. 212 g of the trihydrochloride of the title compound of melting point 196°–198° C. are obtained.

(C) Conversion of the trihydrochloride of the title compound into the monohydrochloride: 212 g of the trihydrochloride are dissolved in 500 ml of water, a solution of 55 g of sodium hydroxide in 55 ml of water is added and the mixture is extracted with three 250 ml portions of methylene chloride. The organic phase is dried over sodium sulphate and filtered. After the solvent has been removed under reduced pressure, the base remains as a colourless oily residue. This is dissolved in 2.5 ml of isopropanol. The solution is mixed, whilst stirring, with a previously prepared solution of 9 g of gaseous hydrogen chloride in 500 ml of isopropanol. The precipitate which thereby forms consists of the monohydrochloride of the title compound. Stirring is continued for 1 hour, and the crystals are then filtered off, washed with three 200 ml portions of isopropanol and dried at 60° C. in a drying chamber for 12 hours. Melting point: 206°–208° C., yield: 164 g.

EXAMPLE 3

1,5-Diphenyl-2-[3-(4-phenylpiperazin-1-yl)-propyl]-pyrazolin-3-one 31.3 g of 1,5-diphenyl-2-(3-chloropropyl)-pyrazolin-3-one (prepared analogously to Example 1A) are dissolved in 300 ml of toluene, and 18.6 g of N-phenylpiperazine and 15.9 g of potassium carbonate are added to the solution. The suspension formed is heated under reflux for 20 hours, whilst stirring. After the reaction solution has been cooled, it is extracted by shaking with water and the organic phase is separated off and concentrated as far as possible under reduced pressure. Dilute hydrochloric acid is added to the residue, and the suspension thereby obtained is extracted with methylene chloride. Dilute sodium hydroxide solution is added to the now clear aqueous phase until the mixture has an alkaline reaction, and the mixture is extracted with ethyl acetate. The organic extract is separated off, dried over sodium sulphate and filtered and the filtrate is evaporated under reduced pressure. The crude 1,5-diphenyl-2-[3-(4-phenylpiperazin-1-yl)-propyl]-pyrazolin-3-one remains as a light yellow oil (41.2 g).

To form the dihydrochloride, this residue is dissolved in isopropanol, and a saturated solution of hydrogen chloride gas in diethyl ether is added dropwise to the solution, whilst stirring. The dihydrochloride, which has precipitated as crystals, is filtered off with suction and rinsed with isopropanol and ether. Melting point: 227°–230° C., yield: 38.7 g.

EXAMPLE 4

1,5-Diphenyl-2-{3-[4-(4-trifluoromethylphenyl)-piperazin-1-yl]-propyl}-pyrazolin-3-one (A) 24.2 g of the 1,5-diphenylpyrazolo-[2,3-b]-dihydrooxazinium chloride prepared according to Example 2A are heated under reflux in 200 ml of isopropanol with 22.8 g of N-formylpiperazine and 2.5 g of potassium bromide for 12 hours. The isopropanol is then distilled off in vacuo and the residue is taken up in toluene. The toluene phase is extracted with dilute hydrochloric acid, dilute sodium hydroxide solution is added to the hydrochloric acid extracts until the mixture has an alkaline reaction, and the mixture is extracted with methylene chloride. The methylene chloride phase is separated off, washed neutral, dried over sodium sulphate and evaporated in vacuo. 1,5-Diphenyl-2-[3-(4-formylpiperazin-1-yl)-propyl]-pyrazolin-3-one is obtained as the residue.

(B) 19.2 g of 1,5-diphenyl-2-[3-(4-formylpiperazin-1-yl)-propyl]-pyrazolin-3-one are dissolved in 200 ml of a mixture of ethanol and 20% strength hydrochloric acid (1:1). The solution is left to stand at room temperature for 12 hours and is then heated under reflux for another 2 hours, and the ethanol is then distilled off in vacuo. Toluene and dilute sodium hydroxide solution are added to the residue. The toluene phase is separated off, washed with water, dried over sodium sulphate and evaporated in vacuo. 1,5-Diphenyl-2-[3-(piperazin-1-yl)-propyl]-pyrazolin-3-one is obtained as the residue.

(C) 13.3 g of the piperazine compound obtained above are dissolved in 150 ml of dimethylformamide, 7 g of potassium carbonate and 8.5 g of 4-trifluoromethylbromobenzene are added to the solution, and the mixture is heated at 120° C. for 16 hours, whilst stirring. The solvent is then substantially stripped off under reduced pressure, the dark brown residue is taken up in dilute hydrochloric acid and the mixture is extracted with ethyl acetate, which can then be discarded. The aqueous phase is subsequently rendered alkaline again and is extracted with methylene chloride. The organic phase is dried over sodium sulphate and filtered over a short silica gel column. After the solvent has been evaporated off, the title compound remains as a colourless viscous oil.

The 1,5-diphenyl-2-[(piperazin-1-yl)-alkyl]-pyrazolin-3-one compounds of the formula I listed in the table which follows can also be prepared from corresponding compounds of the formula II, III or IV by the processes described in Examples 1–4.

| Ex. No. | R₁ | R₂ | R₃ | R₄ | Z | R₅ | Salt | Melting point °C. |
|---|---|---|---|---|---|---|---|---|
| 5 | H | H | H | H | C₂H₄ | 2-Cl—Phen | Di-HCl | 215 |
| 6 | H | H | H | H | n-C₃H₆ | 2-Cl—Phen | Di-HCl | 162–164 |
| 7 | H | H | H | H | n-C₄H₈ | 2-Cl—Phen | Di-HCl | 164–167 |
| 8 | H | H | H | H | n-C₃H₆ | 4-Cl—Phen | HCl—Hydrate | 238–240 |
| 9 | H | H | H | H | n-C₃H₆ | 2-CH₃O—Phen | Ma | 158–160 |
| 10 | H | H | H | H | C₂H₄ | 4-CH₃O—Phen | Base 0.5 n-C₄H₉OCOCH₃ | 105–107 |
| 11 | H | H | H | H | n-C₃H₆ | 4-CH₃O—Phen | Di-HCl | 201–203 |
| 12 | H | H | H | H | n-C₄H₈ | 4-CH₃0—Phen | Base | 74–76 |
| 13 | 4-Cl | H | H | H | n-C₃H₆ | 2-Pyr | HCl | 190–192 |
| 14 | H | H | H | H | n-C₄H₈ | 2-Pyr | HCl | 185–190 |
| 15 | H | H | H | H | C₂H₄ | 3,4-OC₂H₄O—Phen | Base | oil |
| 16 | H | H | 3,4di-CH₃O | H | n-C₃H₆ | Phen | Base | oil |
| 17 | 3-CH₃COO | H | H | H | n-C₃H₆ | Phen | Base | oil |
| 18 | 3-OH | H | H | H | n-C₃H₆ | Phen | Base | oil |
| 19 | H | H | H | H | n-C₄H₈ | Phen | Base | oil |
| 20 | H | 2-CH₃ | H | H | C₂H₄ | Phen | Base | oil |
| 21 | H | H | H | H | n-C₄H₈ | 2-CH₃O—Phen | HCl | 151–152 |
| 22 | H | H | H | H | n-C₃H₆ | 4-F-Phen | Di-HCl | 185–190 (133–135 s) |
| 23 | H | H | H | H | n-C₃H₆ | 4-CH₃O—Phen | Di-HCl | 220–222 |
| 24 | H | H | H | H | n-C₃H₆ | Phen | Base | oil |
| 25 | H | H | H | H | n-C₄H₈ | 3-Pyr | Base | oil |
| 26 | H | H | H | H | C₂H₄ | 4-Pyr | Base | oil |
| 27 | H | H | H | H | n-C₃H₆ | 4-CH₃—2-Pyr | Tri-HCl.H₂O | 203–205 (145 s) |
| 28 | H | H | H | H | n-C₄H₈ | 4-CH₃—2-Pyr | Base | 132–134 |
| 29 | 3-CH₃ | H | H | H | C₂H₄ | Phen | Base | oil |
| 30 | H | H | H | H | n-C₄H₈ | 2-Br—Phen | Base | oil |
| 31 | 3,4-OCH₂O | | 4-Cl | H | n-C₃H₆ | 2-F—Phen | Base | oil |
| 32 | H | H | 3-CH₃ | H | n-C₃H₆ | Phen | Base | oil |
| 33 | H | H | H | H | C₂H₄ | 2-Pyr | Base | oil |
| 34 | H | H | H | H | n-C₃H₆ | 4-Pyr | HCl | 185–190 |
| 35 | H | H | H | H | n-C₃H₆ | 2-Br—Phen | Base | oil |
| 36 | H | H | H | H | n-C₃H₆ | 2-Thien | HCl | 170–175 (d) |
| 37 | H | H | H | H | n-C₃H₆ | 3-Thien | Base | oil |
| 38 | H | H | H | H | n-C₃H₆ | 4-OH—Phen | Base | oil |
| 39 | H | H | H | H | n-C₃H₆ | 3-CF₃—Phen | Di-HCl | 200–212 |
| 40 | H | H | H | H | n-C₃H₆ | 4-CH₃COO—Phen | Base | oil |
| 41 | 4-CH₃ | H | H | H | n-C₃H₆ | 2-Pyr | HCl | 180–182 |
| 42 | H | H | 2-Br | H | n-C₃H₆ | 2-Pyr | Base | 118–120 |
| 43 | H | H | 2-CH₃ | H | n-C₃H₆ | 2-Pyr | Base | 92–94 |
| 44 | H | H | 4-CH₃O | H | n-C₃H₆ | 2-Pyr | Base | oil |
| 45 | H | H | 3-CF₃ | H | n-C₃H₆ | 2-Pyr | Base | oil |
| 46 | 4-CH₃ | H | 2-Br | H | n-C₃H₆ | 2-Pyr | Base | oil |
| 47 | 4-Cl | H | 4-CH₃O | H | n-C₃H₆ | 2-Pyr | Base | oil |
| 48 | H | H | H | H | n-C₃H₆ | 2,6-di-CH₃—Phen | Base | 85–88 |
| 49 | H | H | H | H | n-C₃H₆ | 3,4-di-CH₃O—Phen | Base | 126–127 |
| 50 | H | H | H | H | n-C₃H₆ | 2-CH₃O—4-Cl—Phen | Base | oil |
| 51 | H | H | H | H | n-C₃H₆ | 2-C₂H₅O—Phen | Base | oil |
| 52 | H | H | H | H | n-C₃H₆ | 3-CH₃—Phen | Base | oil |
| 53 | H | H | H | H | n-C₃H₆ | 4-CH₃O-5-Pyr | Base | oil |
| 54 | H | H | H | H | n-C₃H₆ | 4-CH₃—Phen | Base | oil |
| 55 | H | H | H | 4-F | n-C₃H₆ | 2-Pyr | Base | oil |
| 56 | H | H | H | H | n-C₃H₆ | 3,4-O—CH₂—O—Phen | Base | oil |
| 57 | H | H | H | H | n-C₃H₆ | 4-Cl—2-Pyr | Base | oil |
| 58 | H | H | H | H | n-C₄H₉ | 4-F—Phen | Base | oil |
| 59 | 4-CH₃ | H | 2-Cl | H | n-C₃H₆ | 2-Pyr | Base | oil |
| 60 | 4-CH₃O | H | H | H | n-C₃H₆ | 2-Pyr | Base | oil |

Phen = phenyl
HCl = hydrochloride
oil = oily
Pyr = pyridyl
Ma = maleate
d = decomposition
Thien = thienyl
Base = free base
s = softens

EXAMPLE I

Tablets

Tablets having the following composition per tablet are prepared:

| | |
|---|---|
| 1,5-Diphenyl-2-{3-[4-(2-pyridyl)-piperazin-1-yl]-propyl}-pyrazolin-3-one monohydrochloride | 25 mg |

-continued

| | |
|---|---|
| corn starch | 60 mg |
| Lactose | 130 mg |
| Gelatine solution (10% strength solution) | 6 mg |

The active compound, the maize starch and the lactose are thickened with the 10% strength gelatine solution. The paste is comminuted and the granules formed are placed on a suitable metal sheet and dried at 40° C. The dried granules are passed through a comminuting machine, and mixed with the further following auxiliaries in a mixer:

|   |   |
|---|---|
| Talc | 5 mg |
| Magnesium stearate | 5 mg |
| corn starch | 9 mg | and the mixture is then pressed to tablets weighing 240 mg.

We claim:

1. A 1,5-diphenylpyrazolin-3-one compound of the formula I

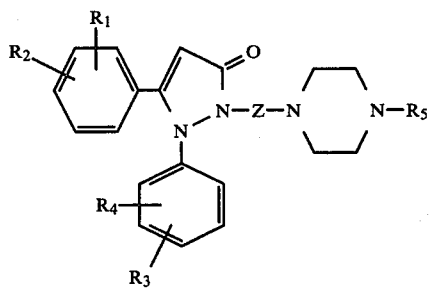

where $R_1$ is a hydrogen or halogen atom, or a lower alkyl, lower alkoxy, hydroxyl, trifluoromethyl or lower alkanoyloxy, $R_2$ is a hydrogen or halogen atom, or a lower alkyl or lower alkoxy, or $R_1$ and $R_2$ are bonded to adjacent carbon atoms and together denote a methylenedioxy or ethylenedioxy, $R_3$ is a hydrogen or halogen atom, or a lower alkyl, lower alkoxy, hydroxy, trifluoromethyl or lower alkanoyloxy, $R_4$ is a hydrogen or halogen atom, or a lower alkyl or lower alkoxy, or $R_3$ and $R_4$ are bonded to adjacent carbon atoms and together denote a methylenedioxy or ethylenedioxy, Z is an alkylene with 2 to 6 carbon atoms, and $R_5$ is an unsubstituted pyridyl, a pyridyl which is monosubstituted by a halogen atom, or a lower alkyl or lower alkoxy, a thienyl or an unsubstituted or substituted phenyl a

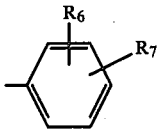

where $R_6$ is a hydrogen or halogen atom, or a lower alkyl, lower alkoxy, hydroxyl, trifluoromethyl or lower alkanoyloxy, and $R_7$ is a hydrogen or halogen atom, or a lower alkyl or lower alkoxy, or $R_6$ and $R_7$ are bonded to adjacent carbon atoms and together denote a methylenedioxy or ethylenedioxy; and acid addition salts thereof.

2. A 1,5-diphenylpyrazolin-3-one compound as claimed in claim 1, where Z, $R_1$, $R_2$, $R_3$ and $R_4$ have the meanings defined in claim 1, and $R_5$ is an unsubstituted or substituted phenyl a

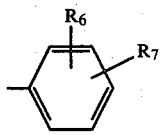

where $R_6$ and $R_7$ have the meanings defined in claim 1.

3. A 1,5-diphenylpyrazolin-3-one compound as claimed in claim 1, where Z, $R_1$, $R_2$, $R_3$ and $R_4$ have the meanings defined in claim 1 and $R_5$ is an unsubstituted pyridyl or a pyridyl which is monosubstituted by a halogen atom or a lower alkyl or lower alkoxy.

4. 1,5-Diphenyl-2-{3-[4-(2-pyridyl)-piperazin-1-yl]-propyl}-pyrazolin-3-one and acid addition salts thereof, according to claim 3.

5. A pharmaceutical composition containing a pharmacologically active amount of a 1,5-diphenyl-pyrazolin-3-one compound as claimed in claim 1 together with one or more pharmaceutically acceptable solid or liquid diluents or carriers.

* * * * *

UNITED STATES PATENT AND TRADEMARK OFFICE
CERTIFICATE OF CORRECTION

PATENT NO.  : 4,442,102

DATED       : April 10, 1984

INVENTOR(S) : Henning Heinemann et al.

It is certified that error appears in the above-identified patent and that said Letters Patent is hereby corrected as shown below:

In the Abstract, the formula should appear as shown below:

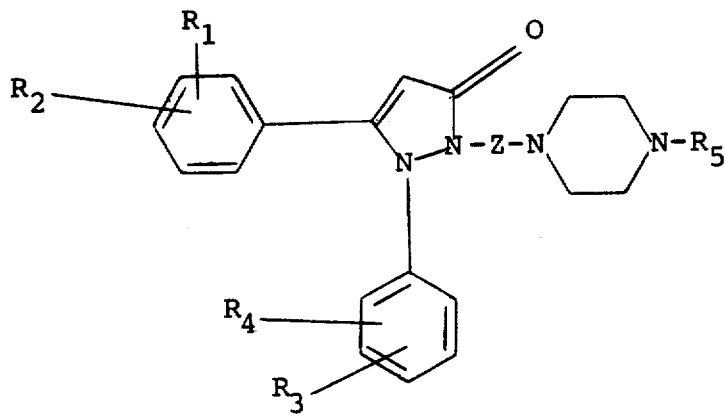

Signed and Sealed this

Twenty-sixth Day of March 1985

[SEAL]

Attest:

DONALD J. QUIGG

Attesting Officer  Acting Commissioner of Patents and Trademarks